Figure 1:
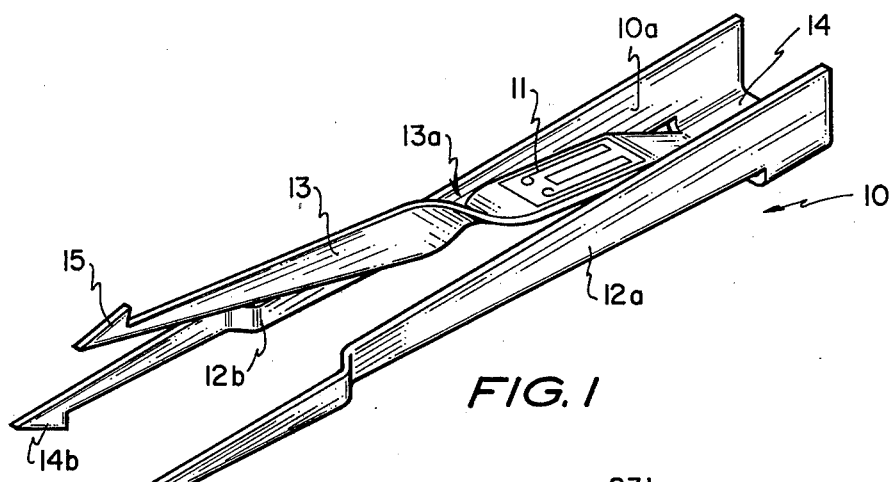

United States Patent [19]

Barker

[11] 4,289,036
[45] Sep. 15, 1981

[54] GAUGE FOR MEASURING THE MOUTH OPENING DISPLACEMENT OF FRACTURE TOUGHNESS TEST SPECIMENS

[75] Inventor: Lynn M. Barker, Salt Lake City, Utah

[73] Assignee: Terra Tek, Inc., Salt Lake City, Utah

[21] Appl. No.: 133,524

[22] Filed: Mar. 24, 1980

[51] Int. Cl.³ .............................................. G01L 1/22
[52] U.S. Cl. ................................... 73/799; 73/862.65
[58] Field of Search ................. 73/799, 141 R, 141 A, 73/826, 834, 849

[56] References Cited

U.S. PATENT DOCUMENTS 1,557,341 10/1925 Scalbom ........................... 73/141 A
4,003,246 1/1977 Cain ....................................... 73/799

Primary Examiner—Jerry W. Myracle
Attorney, Agent, or Firm—M. Reid Russell

[57] ABSTRACT

The gauge of the present invention consists of a three-pronged spring clip for arrangement between the grips of a conventional grip-loading fracture specimen loading machine, which grips are inserted into the mouth of a standard slotted fracture toughness test specimen, the gauge to monitor the specimen mouth opening displacement thereof during a test for fracture toughness. The spring clip preferably is formed from a single sheet of material that is bent appropriately to produce two aligned legs or prongs with a center leg or prong there between. In operation the outside prongs are essentially stationary while the center prong is arranged to flex with respect to grip movement apart, which center movement is sensed electrically by a strain gauge secured thereto at its point of bending.

4 Claims, 7 Drawing Figures

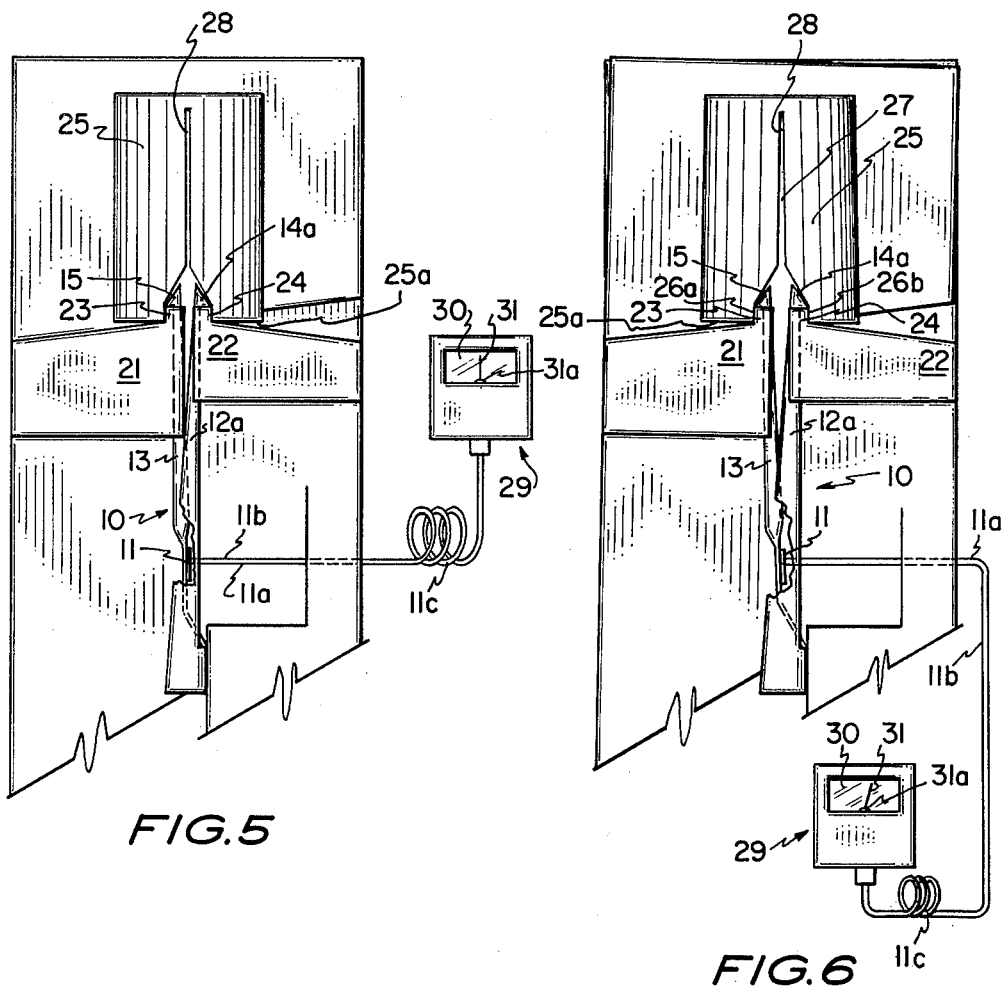
FIG.5
FIG.6
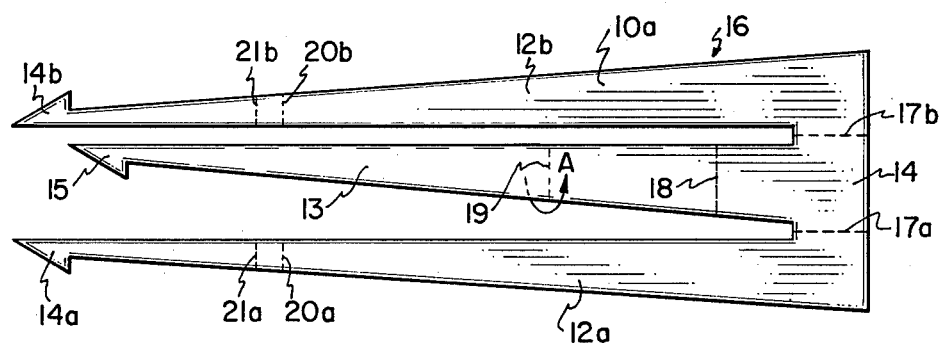
FIG.7

GAUGE FOR MEASURING THE MOUTH OPENING DISPLACEMENT OF FRACTURE TOUGHNESS TEST SPECIMENS

The present invention relates to devices for measuring mouth opening displacement of a fracture toughness test specimen during a test thereon for fracture toughness.

Heretofore, previous designs of devices for measurement of mouth opening displacement have involved complicated designs of clip gauges. An example of one such clip gauge design is shown and described with respect to an American Society of Testing and Material Standard (ASTM) identified as Method "E399". The gauge device described in the above-cited standard includes a type of clip gauge that must be physically attached to a specimen, and is such as to require machining to close tolerances to avoid hysteresis and non-linearity effects in the gauge output. The present invention, unlike that clip of the standard, consists of a single spring clip made from a single piece of sheet metal. Also, it includes legs or prongs that are arranged to fit within appropriate grooves formed in grips or jaws of a standard test machine to extend prong ends from opposite grip faces to engage the specimen when the grips are fitted into a mouth opening of a slotted test specimen. The prong ends thereby achieve a metal to metal attachment to the specimen across the specimen slot.

An example of a fracture specimen loading machine that incorporates grips suitable for accommodating the gauge of the present invention, is shown in a U.S. patent application made by the present inventor as a co-inventor, filed Nov. 9, 1978, Ser. No. 959,202, now U.S. Pat. No. 4,198,870, for a Constant Point of Load Application Fracture Specimen Loading Machine.

Within the knowledge of the inventor, there has not heretofore existed a gauge device suitable for installation with test machine grips into the mouth of a slotted specimen for measurement of the mouth opening thereof during a test for fracture toughness. The present invention is, therefore, believed to be both novel and unique and a significant improvement in the art.

It is, therefore, a general object of the present invention to provide a gauge device for accurately and continuously measuring the mouth opening displacement across the slot of a slotted fracture toughness test specimen during fracture toughness testing thereof.

It is an additional object of the present invention to provide a gauge device that is compatible for use with a standard specimen fracture loading machine that includes grips that are installable within a mouth of a slotted test specimen and are moved apart to fracture that specimen.

It is an additional object of the present invention to provide a gauge device that includes a clip gauge manufactured from a single sheet of material which avoids hysteresis and non-linearity effects on an output thereof, and that is automatically installed in a slotted test specimen mouth to accurately measure specimen mouth opening when the specimen is fitted onto the grips.

In accordance with the above objects, the present invention in a gauge for measuring a mouth opening displacement of fracture toughness test specimens includes a three-pronged clip gauge that is preferably formed as a single integral unit by appropriate stamping and bending of a sheet of metal material to form a base wherefrom three prongs extend in essentially parallel planes. Two of the prongs referred to herein as outside prongs are aligned to function as stationary prongs with the third center prong arranged to flex relative thereto. The bending of the center prong is essentially concentrated at its junction with the base whereat a standard strain gauge is secured. The strain gauge senses flexure thereacross by a change in electrical resistance, that change in resistance shown by connecting a meter or the like across that resistance as a visual display.

In use, the three prongs are fitted through appropriate grooves formed in grips of a standard grip loading fracture toughness specimen testing machine. The prongs are arranged such that barbed ends extend beyond the grips to engage opposite sides of the slot mouth of a standard slotted fracture toughness test specimen. The prong barbed ends thereby engage both faces of the specimen slot to provide translation of specimen mouth opening through the center prong to a strain gauge installed thereto. Prior to specimen loading, the center prong is in a loaded state and unloads, relaxing, as described, as the grips are moved apart.

By fabricating the clip gauge from a single piece of relatively thin sheet steel, or other suitable metal material, it is possible to obtain a linear output with no hysteresis from flexure of the center prong. In addition, such construction minimizes the weight of the gauge, thus maximizing its stability when installed in a test specimen mouth. Further, the thinness of the prongs of the gauge and the minimum contact of the barbed ends thereof to the specimen provides for a good thermal isolation with respect to the strain gauge, allowing thereby for the specimen to be subject to various temperature conditions without affecting the accuracy of the strain gauge output.

Figure 2:
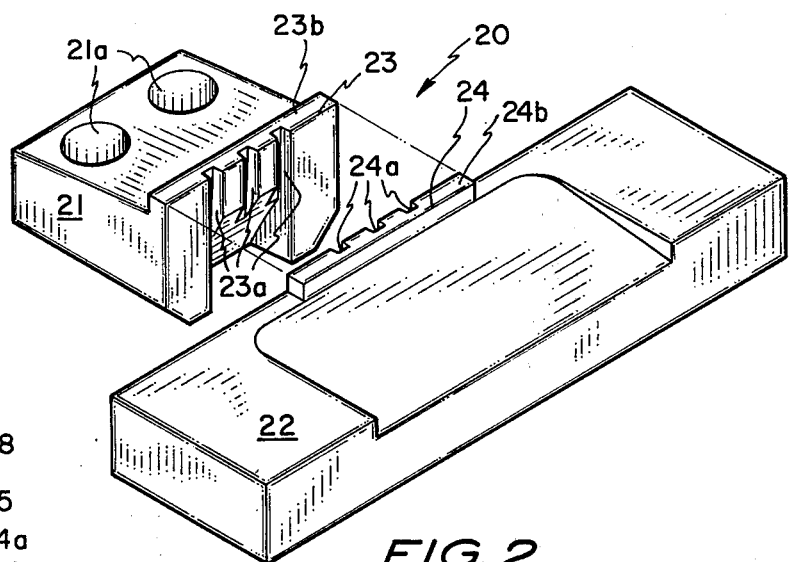
Figure 4:
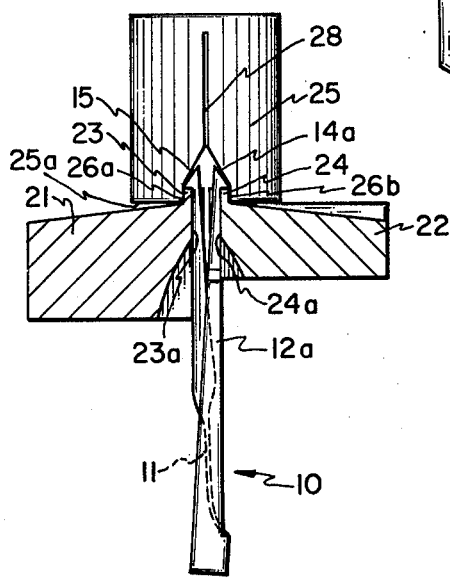
Figure 3:
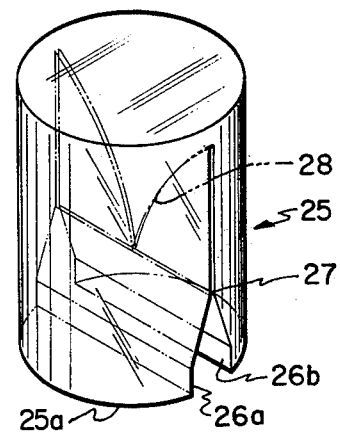

FIG. 1, is a side elevation perspective view of the gauge of the present invention shown as a three-pronged spring clip with two outside prongs and a center prong that all extend in essentially parallel planes from a base, the center prong shown to include a strain gauge secured across a flexure region thereof;

FIG. 2, a perspective view of load grips of a standard fracture toughness test machine for subjecting a slotted fracture toughness test specimen to opposing load forces across the specimen mouth, which grips are shown slotted appropriately to accommodate the prongs of the gauge of FIG. 1;

FIG. 3, a side elevation view of a preferred fracture toughness test specimen that is shown slotted longitudinally to leave as a slot remainder a V-shaped root, which specimen is shown as having lateral grip grooves formed across opposite slot faces to accommodate the grips of FIG. 2 fitted thereto;

FIG. 4, a side elevation view showing the gauge of FIG. 1 and the grips of FIG. 2 installed within the mouth of the slotted specimen of FIG. 3, which grips are shown broken away;

FIG. 5, shows a view like that of FIG. 4, excepting the grips are shown intact, and further includes an electrical connection to the strain gauge portion of the gauge of an appropriate signal conditioner and electrical meter;

FIG. 6, is a view like that of FIG. 5 only showing the grips having moved apart, relaxing the prongs of the gauge away from one another, changing the resistance across the strain gauge as reflected by movement of the meter needle; and FIG. 7, shows a flattened folded-out view of the clip gauge of the gauge FIG. 1 illustrating with broken lines, where folds or bends are made to form the clip gauge with an Arrow A showing the center prong as twisted through approximately ninety degrees (90°).

FIG. 1 illustrates a preferred arrangement of gauge 10 for measuring the mouth opening displacement of fracture toughness test specimens hereinafter referred to as "gauge". In FIG. 1, the gauge 10, includes a strain gauge 11 that senses changes in electrical resistance thereacross that is installed to a clip gauge 10a. The clip gauge 10a is shown in FIG. 7 formed from a single flat section 16 of an elastic metal material, such as a thin gauge spring steel, that has appropriate characteristics of strength and flexibility that is bent, as shown by broken lines 17a, 17b, 18 and 19, and twisted, as shown by Arrow A. Thereby outside prongs 12a and 12b and center prong 13 as shown best in FIG. 1, are formed so as to act as bars that resist bending across wide portions thereof. Prongs 12a, 12b and 13 all include barb-type ends 14a, 14b and 15, respectively that have pointed ends that face oppositely, to engage, as will be described with respect to FIGS. 4 through 6, surfaces of grip grooves of a fracture toughness test specimen.

Shown in FIG. 7, the flat section 16 has been stamped into the configuration of the clip gauge 10a. With reference to that section 16, the parallel outside prongs 12a and 12b are formed by bending sides of the section upwardly to ninety degrees (90°) along broken lines 17a and 17b, respectively. The center prong 13 is formed, in turn, by bending the prong across base 14, along broken lines 18 and 19, and then twisting the center prong end section through ninety degrees (90°) thereof, as shown at Arrow A. The outside and center prongs thereby are formed to have wide surfaces in planes that are approximately parallel to a force to be applied to fracture a test specimen, as will be explained in detail later herein. The outside parallel prongs 12a and 12b are bent oppositely at broken lines 20a and 20b and 21a and 21b, dog legging outwardly and inwardly to provide a reinforcement thereof to resist collapse of the outside prongs when fitted to a test specimen. So arranged, prongs 12a and 12b tend to remain fixed, with movement of test machine grips to split a test specimen as will be explained later herein, moving the center prong 13 only and is thereby resolved in the strain gauge 11.

Center prong 13, as described hereinabove, is twisted at Arrow A, as shown in FIG. 7, and at 13a as shown in FIG. 1, to form a bar that resists bending thereacross. So arranged, vertical movement of center prong 13 responsive to movement of the grips apart, is concentrated in a center prong flat area between the bends made along broken lines 18 and 19 whereto the strain gauge 11 is secured. Thereby, the flexing of center prong 13 is concentrated into the area whereto strain gauge 11 is attached. As will be explained with respect to FIGS. 5 and 6, flexing of the strain gauge 11 is translated into changes in electrical resistance to provide a measure of the test specimen mouth during fracture toughness testing thereof.

FIG. 2, shows a set of grips 20 that should be understood to be attached to a standard fracture specimen loading machine, not shown, that provides a controlled movement apart of the grips to fracture a slotted test specimen mounted onto the grips. As shown in FIG. 2, a first grip base 21 preferably includes holes 21a to accommodate screws or like fastening devices for attachment to a movable pivot arm of a fracture specimen loading machine, not shown, that is preferably like the arrangement shown in my prior cited application for U.S. patent, Ser. No. 959,202. Aligned and spaced apart from grip base 21, as also shown in FIG. 2, is a second grip base 22 that is preferably installed in an appropriate saddle or like arrangement of the fracture specimen loading machine, not shown. Second grip base 22 can thereby either be maintained in a stationary attitude, with the first grip base 21 moved apart therefrom, or can be arranged on a second movable pivot arm to move apart from that first grip base 21. The respective first and second grip bases 21 and 22 have formed or secured thereto, grips 23 and 24, respectively. Shown best in FIGS. 4 through 6, with grips 23 and 24 closed together, a slotted fracture toughness test specimen 25, hereinafter referred to as specimen, as shown in FIG. 3, can be mounted thereover. As shown in FIG. 3, the specimen 25 preferably has a longitudinal slot 27 formed therein leaving a v-shaped root 28. The slot 27, proximate to a specimen face 25a has grip groove faces 26a and 26b machined thereacross that are essentially parallel to one another to fit over the grips 23 and 24. The grip groove faces 26a and 26b, in turn, slant towards one another at 27a and 27b and terminate in slot 27.

As shown best in FIG. 2, grips 23 and 24 have, respectively, lateral slots 23a and 24a formed therein to accomodate the outside and center prongs 12a, 12b and 13 of gauge 10 installed therein. The installation of gauge 10 to grips 23 and 24, is shown best in FIGS. 4 through 6. Shown therein the outside and center prong barbed ends 14a, 14b and 15 will extend beyond grips 23 and 24, such that the pointed ends thereof will engage the parallel specimen grip groove faces 26a and 26b just below the slanting portions 27a and 27b of the slot 27. Thereby, simultaneously, the grips 23 and 24 and barbed prong ends 14a, 14b and 15 will make a direct metal-to-metal contact with the specimen 25 such that, movement apart of the grips to open the specimen mouth across slot 27 will be translated directly through the center prong 13 into strain gauge 11. Of course, as shown best in FIG. 4, center prong 13 is flexed or loaded towards prongs 14a and 14b when the grips 23 and 24 are together. The loading is released as the grips are moved apart to fracture the specimen 25 and that change in loading is sensed at strain gauge 11.

FIGS. 5 and 6 illustrate the operation of strain gauge 11. FIG. 5, which is essentially like FIG. 4, but further includes wires 11a and 11b that connect the strain gauge 11 through a signal conditioner 11c to a meter 29. The meter 29 includes a face 30, with an appropriate graduated scale marked thereon, and includes a pivoting needle or pointer 31 that travels responsive to changes in resistance across the strain gauge 11, across the graduated scale on face 30 around a pointer pivot 31a.

FIG. 5, shows specimen 25 fitted onto grips 23 and 24 with the parallel grip groove faces 26a and 26b shown engaging barbed prong ends 15 and 14a. So arranged, with no loading force on the grips, the meter pointer 31 would be in one position as illustrated in FIG. 5. Movement of grips 23 and 24 away from one another would relax the center prong 13 away from outside prongs 12a and 12b to change the electrical resistance across strain gauge 11 as illustrated by a change in position of pointer 31 as shown in FIG. 6. Such resistance change is then transmitted through wires 11a and 11b to a signal conditioner 11c that operates meter 29. The change in pointer 31 position reflects the change in resistance attributable to specimen mouth opening. Therefrom, by observing movement of pointer 31 it is possible to continuously measure specimen mouth opening during the fracturing of the specimen.

The particular arrangement of grips 23 and 24 and grip bases 21 and 22, with slots 23a and 24 formed thereacross is preferred for positioning of the outside and center prongs 12a, 12b and 13, to specimen 25. However, it should be obvious that any type of grip configuration arranged to accommodate both the prongs of gauge 10 and specimen so as to provide a direct contact of the prongs of the gauge to the specimen across a slot mouth thereof would be suitable. While the present invention provides for movement of a center prong only as a single grip is moved, a different configuration of a fracture toughness specimen loading machine where both grips and the center and outside prongs therewith are simultaneously moved apart could also utilize the gauge 10 as described.

While the preferred configuration of gauge 10 includes two outside prongs and a center prong, it should be understood that the present disclosure is made by way of example and that variations are possible without departing from the subject matter coming within the scope of the following claims, which I regard as my invention.

What is claimed is:

1. A gauge for measuring the mouth opening displacement of fracture toughness test specimens consisting of,
   a clip gauge formed from a single sheet of suitable material that is cut and bent appropriately to form a base wherefrom center and outside prongs extend in essentially parallel planes;
   means secured to the prong ends opposite to said base for directly engaging opposite slot faces across a test specimen mouth;
   strain gauge means secured to said center prong so as to sense flexure thereof as a change in electrical resistance; and
   means, connected to said strain gauge means, for translating changes in electrical resistance to specimen mouth opening displacement.

2. A gauge as recited in claim 1, wherein,
   the clip gauge is formed to include two outside prongs with a single center prong arranged to flex therebetween, which outside and center prongs are bent and twisted appropriately to present surfaces that resist bending thereacross such that movement at said prong ends causes bending in an area of said center prong proximate to its connection to said base; and
   the strain gauge means is secured to said center prong in said area of said center prong proximate to its connection to said base.

3. A gauge as recited in claim 1, wherein
   the means secured to the outside and center prong ends are oppositely facing barbed ends.

4. A gauge as recited in claim 1, wherein the means for translating changes in electrical resistance to specimen mouth opening displacement include
   means for conditioning said change in resistance to operate a movement of a meter; and
   a meter operated by said conditioned change in resistance to provide a display of said specimen mouth opening.

* * * * *